(12) United States Patent
Macina et al.

(10) Patent No.: US 6,949,339 B1
(45) Date of Patent: Sep. 27, 2005

(54) METHOD OF DIAGNOSING, MONITORING, AND STAGING COLON CANCER

(75) Inventors: Roberto A. Macina, San Jose, CA (US); Fei Yang, San Diego, CA (US); Yongming Sun, San Jose, CA (US)

(73) Assignee: diaDexus, Inc., South San Francisco, CA (US)

( * ) Notice: Subject to any disclaimer, the term of this patent is extended or adjusted under 35 U.S.C. 154(b) by 0 days.

(21) Appl. No.: 09/700,769

(22) PCT Filed: May 12, 1999

(86) PCT No.: PCT/US99/10498

§ 371 (c)(1),
(2), (4) Date: Jan. 4, 2001

(87) PCT Pub. No.: WO99/60161

PCT Pub. Date: Nov. 25, 1999

Related U.S. Application Data
(60) Provisional application No. 60/086,266, filed on May 21, 1998.

(51) Int. Cl.[7] .................................................. C12Q 1/70
(52) U.S. Cl. .............................. 435/6; 435/4; 435/7.21; 435/7.23; 436/63; 436/64; 536/1.11; 536/18.7; 536/22.1; 536/23.1; 536/23.5
(58) Field of Search ............................. 435/4, 6, 7.21, 435/7.23; 536/1.11, 18.7, 22.1, 23.1, 23.5; 436/63, 64; 530/300, 350

(56) References Cited

U.S. PATENT DOCUMENTS

| | | | |
|---|---|---|---|
| 4,690,914 A | 9/1987 | Callut et al. ................. | 502/400 |
| 5,585,103 A | 12/1996 | Raychaudhuri et al. ... | 424/278.1 |
| 5,733,748 A | 3/1998 | Yu et al. | |
| 5,929,033 A | 7/1999 | Tang et al. | |
| 5,985,270 A | 11/1999 | Srivastava ............... | 424/93.71 |
| 2003/0109690 A1 | 6/2003 | Ruben | |

FOREIGN PATENT DOCUMENTS

| | | |
|---|---|---|
| WO | WO 96/39419 A1 | 12/1996 |
| WO | WO 96/39419 A1 | 12/1996 |
| WO | WO 97/42506 | 11/1997 |
| WO | WO 98/44133 A1 | 10/1998 |
| WO | WO 98/44159 | 10/1998 |
| WO | WO 99/01020 A2 | 1/1999 |
| WO | WO 99/24463 A2 | 5/1999 |
| WO | WO 99/25828 A1 | 5/1999 |
| WO | WO 99/47658 A1 | 9/1999 |
| WO | WO 99/53051 A2 | 10/1999 |
| WO | WO 99/55858 A2 | 11/1999 |
| WO | WO 99/60161 A1 | 11/1999 |
| WO | WO 99/63088 A2 | 12/1999 |
| WO | WO 00/07632 | 2/2000 |
| WO | WO 00/12708 A2 | 3/2000 |
| WO | WO 00/28031 A2 | 5/2000 |
| WO | WO 00/32221 A2 | 6/2000 |
| WO | WO 00/37643 A2 | 6/2000 |

OTHER PUBLICATIONS

Bánfi et al., "A Mammalian $H^+$ Channel Generated Through Alternative Splicing of the NADPH Oxidase Homolog NOH–1", Science 2000 287:138–142.
NCBI Genbank Accession No. AF127763 [gi:5031251], Jun. 10, 1999 through Oct. 29, 1999 (with revision history).
NCBI Genbank Accession No. AF166327 [gi:6672077], Jan. 6, 2000 (with revision history).
NCBI Genbank Accession No. AF166328 [gi:6672079], Jan. 6, 2000 (with revision history).
NCBI Genbank Accession No. NM_013955 [gi:7669509], Apr. 28, 2000 thorugh Feb. 6, 2001 (with revision history).
NCBI Genbank Accession No. NM_007052 [gi:6631096], Sep. 16, 1999 through Feb. 6, 2001 (with revision history).
Arbiser et al., Reactive oxygen generated by Nox1 triggers the angiogenic switch, PNAS, Jan. 22, 2002, Vol 99, no 2, pp 715–720.
Lambeth et al., Novel homologs of gp91phox, TiBS, 2000, 25, pp 459–461.
Shinozaki et al., Upregulation of Reg 1alpha and GW112 in the epithelium of inflamed colonic mucosa.Gut. 2001 May; vol. 48(5):623–9.
Suh et al., Cell transformation by the superoxide–generating oxidase Mox1, Nature, Sep. 2, 1999, Vol 401, pp 79–82.
Database Genebank, Accession No. XP_010073, NCBI, NADPH oxidase 1 isoform long [Homo sapiens], Aug. 27, 2001, see sequence.
Database Genebank, Accession No. NP_008983, Shu et al., NADPH oxidase 1 isoform long; mitogenic oxidase (pyridine nucleotide–dependent superoxide–generating); NADPH oxidase homolog–1 [Homo sapiens] Feb. 3, 2001, see sequence.
Database Genebank, Accession No. CAB06073,Lloyd, D, dJ146H21.2 (similar to Cytochrome B–245 heavy chain) [Homo Sapiens], Nov. 23, 1999, see sequence.
Database Genebank, Accession No. NP_098249,Suh et al., NADPH oxidase 1 isoform long; mitogenic oxidase (pyridine nucleotide–dependent superoxide–generating); NADPH oxidase homolog–1 [Homo sapiens], Feb. 3, 2001, see sequence.
Database Genebank, Accession No. AK000683, Tanigami et al., Homo sapiens cDNA FLJ20676 fis, clone KAIA4294, highly similar to AF097021 Homo sapiens GW112 protein, Feb. 22, 2000, see sequence.
Database Genebank, Accession No. Q9WV87,Suh et al., NADPH oxidase homolog 1 (NOX–1) (NOH–1) (NADH/NADPH mitogenic oxidase subunit P65–MOX) (Mitogenic oxidase 1) (MOX1), May 30, 2000, see sequence.
Database Genebank, Accession No. O46522,Davis, Cytochrome B–245 heavy chain (P22 phagocyte B–cytochrome) (neutrophil cytochrome B, 91 kDa polypeptide) . . . May 30, 2000, see sequence.

*Primary Examiner*—Alana M. Harris
(74) *Attorney, Agent, or Firm*—Licata & Tyrrell P.C.; Nathan P. Letts

(57) ABSTRACT

The present invention provides a new method for detecting, diagnosing, monitoring, staging, and prognosticating colon cancer.

12 Claims, No Drawings

SEQUENCE LISTING

<160> NUMBER OF SEQ ID NOS: 10

<210> SEQ ID NO 1
<211> LENGTH: 487
<212> TYPE: DNA
<213> ORGANISM: Homo sapien

-continued

```
<400> SEQUENCE: 1
tctgcatctg gccctcccag tgcacctgtt caatcccagc ycctccctga cctgtacaaa        60
tacacctgag gaccggctcg agcccagact tcctgcccct gctctgcact ctcaggtatt       120
ccctgctctt actccaaaaa gatggaccca ggtccgaagg ggcactgcca ctgtgggggg       180
catggccatc ctccaggtca ctgcgggcga acccctggcc atggcccagg gccctgcggg       240
ccaccccctg gccatggccc agggccctgc gggcaacccc ctggccatgg cccagggccc       300
tgcgggcctc cccctggcca tgcccaggt cacccacccc ctggtccaca tcactgagga       360
agtagaagaa aacaggacac aagatggcaa gcctgagaga attgcccagc tgacctggaa       420
tgaggcctaa accacaatct tctcttccta ataaacagcc tcctagaggc cacattctat       480
tctttaa                                                                 487

<210> SEQ ID NO 2
<211> LENGTH: 739
<212> TYPE: DNA
<213> ORGANISM: Homo sapiens
<220> FEATURE:
<221> NAME/KEY: misc_feature
<222> LOCATION: (693)..(693)
<223> OTHER INFORMATION: n=a, c, g or t
<220> FEATURE:
<221> NAME/KEY: misc_feature
<222> LOCATION: (698)..(699)
<223> OTHER INFORMATION: n=a, c, g or t
<220> FEATURE:
<221> NAME/KEY: misc_feature
<222> LOCATION: (703)..(705)
<223> OTHER INFORMATION: n=a, c, g or t
<220> FEATURE:
<221> NAME/KEY: misc_feature
<222> LOCATION: (708)..(708)
<223> OTHER INFORMATION: n=a, c, g or t
<220> FEATURE:
<221> NAME/KEY: misc_feature
<222> LOCATION: (710)..(716)
<223> OTHER INFORMATION: n=a, c, g or t
<220> FEATURE:
<221> NAME/KEY: misc_feature
<222> LOCATION: (718)..(718)
<223> OTHER INFORMATION: n=a, c, g or t
<220> FEATURE:
<221> NAME/KEY: misc_feature
<222> LOCATION: (723)..(726)
<223> OTHER INFORMATION: n=a, c, g or t
<220> FEATURE:
<221> NAME/KEY: misc_feature
<222> LOCATION: (728)..(728)
<223> OTHER INFORMATION: n=a, c, g or t
<220> FEATURE:
<221> NAME/KEY: misc_feature
<222> LOCATION: (732)..(732)
<223> OTHER INFORMATION: n=a, c, g or t
<220> FEATURE:
<221> NAME/KEY: misc_feature
<222> LOCATION: (737)..(737)
<223> OTHER INFORMATION: n=a, c, g or t

<400> SEQUENCE: 2
tctgaaactg tcagttccac cagcactgct tggatactgg taagtttcca gggggctgct        60
ttgcatctga aactgtcagc cccagaatgt tgacagtcgc tctcctagcc cttctctgtg       120
cctcagcctc tggcaatgcc attcaggcca ggtcttcctc ctatagtgga gagtatggaa       180
gtggtggtgg aaagcgattc tctcattctg gcaaccagtt ggacggcccc atcaccgccc       240
tccgggtccg agtcaacaca tactacatcg taggtcttca ggtgcgctat ggcaaggtgt       300
ggagcgacta tgtgggtggt cgcaacggag acctggagga gatctttctg caccctgggg       360
```

```
aatcagtgat ccaggtttct gggaagtaca agtggtacct gaagaagctg gtatttgtga    420
cagacaaggg ccgctatctg tcttttggga aagacagtgg cacaagtttc aatgccgtcc    480
ccttgcaccc caacaccgtg ctccgcttca tcagtggccg gtctggttct ctcatcgatg    540
ccattggcct gcactgggat gtttacccca ctagctgcag cagatgctga gcctcctctc    600
cttggcaggg gcactgtgat gaggagtaag aactccctta tcactaaccc ccatccaaat    660
ggctcaataa aaaatatggt ttaaggctaa aanaaaanng gannnaanan nnnnnntnca    720
aannnnantt cncctgnta                                                 739

<210> SEQ ID NO 3
<211> LENGTH: 428
<212> TYPE: DNA
<213> ORGANISM: Homo sapiens
<220> FEATURE:
<221> NAME/KEY: misc_feature
<222> LOCATION: (392)..(392)
<223> OTHER INFORMATION: n=a, c, g or t

<400> SEQUENCE: 3
aattgtccgg ggtcaaacag aggagagcat gaatgagagt catcctcgca agtgtgcaga     60
gtcttttgag atgtgggatg atcgtgactc ccactgtagg cgccctaagt ttgaagggca    120 tcccctgag tcttggaagt ggatccttgc accggtcatt ctttatatct gtgaaaggat     180
cctccggttt taccgctccc agcagaaggt tgtgattacc aaggttgtta tgcacccatc    240
caaagttttg gaattgcaga tgaacaagcg tggcttcagc atggaagtgg ggcagtatat    300
ctttgttaat tgcccctcaa tctctctcct gggaatggca tccttttact ttgacctctg    360
ctccagagga agatttcttc ttcattcata tncgagcagc aggggacttg acagaaaatc    420
tataaggg                                                            428

<210> SEQ ID NO 4
<211> LENGTH: 1347
<212> TYPE: DNA
<213> ORGANISM: Homo sapiens

<400> SEQUENCE: 4
ggaaaacccc tgagcacaaa gcaagaggca tcgaagcccc ctcggggatg cccgcaagcc     60 aacagggtg tcgtgcggtg ggagtacttc cgcctgcgtc ctctgcggtt cagggcccca    120
gacgagcccc agcaggccca agtcccccat gtctggggct gggaggtggc tggggccct   180 gcactgaggc tgcagaagtc ccagtcatct gatctgctgg aaagggagag ggagagtgtc    240
ctgcgccggg agcaagaggt ggcagaggag cggagaaatg ctctcttccc agaggtcttc    300
tccccaacgc cagatgagaa ctctgaccag aactccagga gctcctccca ggcatccggc    360
atcacgggca gttactcggt gtctgagtct cccttcttca gccccatcca cctacactca    420
aacgtggcgt ggacagtgga agatccagtg gacagtgctc ctcccgggca gagaaagaag    480
gagcaatggt acgctggcat caaccccctcg gacggtatca actcagaggt cctggaagcc    540
atacgggtga cccgtcacaa gaacgccatg gcagagcgct gggaatcccg catctacgcc    600
agtgaggagg atgactgagc ctcggggatgg ggcgcccacc cctgccctg ccctgaccct    660 cgtgggaact gccaagacca tcgccaagcc cccaccctag gaaatgggtc ctaggtccag    720
gatccaagaa ccacagctca tctgccaaca atcccaccat gggcacattt gggactgttg    780 ggttttcgt ttccgtttct atcttccttt agaaatgttt ctgcctttgg ggtctaaagc     840
```

-continued

| | |
|---|---|
| ttttggggat gaaatgggga cccctgctga ttctttctgc ttctaagact ttgccaaatg | 900 |
| ccctgggtct aagaaagaaa gagacccgct cctccacttt caggtgtaat ttgcttccgc | 960 |
| tagtctgagg gcagagggac cggtcaaaga gggtggcaca gatcgcagca ccttgagggg | 1020 |
| ctgcgggtct gagggaggag acactcagct cctccctctg agaagtccca agctgagagg | 1080 |
| ggagacctgc cccttccaa ccctgggaaa ccatccagtc tgaggagga ggccaaactc | 1140 |
| ccagtgctgg gggtccctgt gcagccctca aaccccttcac cttggtgcac ccagccacac | 1200 |
| ctggtggaca caaagctctc acatcgatag gatcccatga ggatggtccc cttcacctgg | 1260 |
| gagaaaagtg acccagttta ggagctggag ggggtctttt gtcccccacc cccaaactgc | 1320 |
| cctgaaataa acctggagtg agctgcc | 1347 |

<210> SEQ ID NO 5
<211> LENGTH: 1249
<212> TYPE: DNA
<213> ORGANISM: Homo sapiens
<220> FEATURE:
<221> NAME/KEY: misc_feature
<222> LOCATION: (1034)..(1056)
<223> OTHER INFORMATION: n=a, c, g or t

<400> SEQUENCE: 5

| | |
|---|---|
| ggcagagcct gcgcagggca ggagcagctg gcccactggc ggcccgcaac actccgtctc | 60 |
| accctctggg cccactgcat ctagaggagg gccgtctgtg aggccactac ccctccagca | 120 |
| actgggaggt gggactgtca gaagctggcc cagggtggtg gtcagctggg tcagggacct | 180 |
| aacggcacct ggctgggacc acctcgcctt ctccatcgaa gcagggaag tgggagcctc | 240 |
| gagcccctcgg gtggaagctg accccaagcc acccttcacc tggacaggat gagagtgtca | 300 |
| ggtgtgcttc gcctcctggc cctcatcttt gccatagtca cgacatggat gtttattcga | 360 |
| agctacatga gcttcagcat gaaaaccatc cgtctgccac gctggctggc ctcgcccacc | 420 |
| aaggagatcc aggttaaaaa gtacaagtgt ggcctcatca gccctgccc agccaactac | 480 |
| tttgcgttta aaatctgcag tggggccgcc aacgtcgtgg gccctactat gtgctttgaa | 540 |
| gaccgcatga tcatgagtcc tgtgaaaaac aatgtgggca gaggcctaaa catcgccctg | 600 |
| gtgaatggaa ccacgggagc tgtgctggga cagaagtcat tgacatgta ctctggagat | 660 |
| gttatgcacc tagtgaaatt ccttaaagaa attccggggg gtgcactggt gctggtggcc | 720 |
| tcctacgacg atccagggac caaaatgaac gatgaaagca ggaaactctt ctctgacttg | 780 |
| gggagttcct acgcaaaaca actgggcttc cgggacagct gggtcttcat aggagccaaa | 840 |
| gacctcaggg gtaaaagccc ctttgagcag ttcttaaaga acagcccaga cacaaacaaa | 900 |
| tacgagggat ggccagagct gctggagatg gagggctgca tgccccccgaa gccattttag | 960 |
| ggtggctgtg gctcttcctc agccaggggc ctgaagaagc tcctgcctga cttaggagtc | 1020 |
| agagcccggc aggnnnnnnn nnnnnnnnnn nnnnnntgct gcgtggaagg tgctgcaggt | 1080 |
| ccttgcacgc tgtgtcgcgc ctctcctcct cggaaacaga accctcccac agcacatcct | 1140 |
| acccggaaga ccagcctcag agggtccttc tggaaccagc tgtctgtgga gagaatgggg | 1200 |
| tgctttcgtc agggactgct gacggctggt cctgaggaag acaaactg | 1249 |

<210> SEQ ID NO 6
<211> LENGTH: 1220
<212> TYPE: DNA
<213> ORGANISM: Homo sapiens

<400> SEQUENCE: 6

-continued

```
gctttctgca cctcattcca catcaggagc gtttttggag aaagctgcac tctgttgagc      60
tccagggcgc agtggaggga gggagtgaag gagctctctg tacccaagga aagtgcagct     120
gagactcaga caagattaca atgaaccaac tcagcttcct gctgtttctc atagcgacca     180
ccagaggatg gagtacagat gaggctaata cttacttcaa ggaatggacc tgttcttcgt     240
ctccatctct gcccagaagc tgcaaggaaa tcaaagacga atgtcctagt gcatttgatg     300
gcctgtattt tctccgcact gagaatggtg ttatctacca gaccttctgt gacatgacct     360
ctggggtgg cggctggacc ctggtggcca gcgtgcacga aatgacatg cgtgggaagt       420
gcacggtggg cgatcgctgg tccagtcagc agggcagcaa agcagtctac ccagagggg      480
acggcaactg ggccaactac aacacctttg gatctgcaga ggcggccacg agcgatgact     540
acaagaaccc tggctactac gacatccagg ccaaggacct gggcatctgg cacgtgccca     600
ataagtcccc catgcagcac tggagaaaca gctccctgct gaggtaccgc acggacactg     660
gcttcctcca gacactggga cataatctgt ttggcatcta ccagaaatat ccagtgaaat     720
atggagaagg aaagtgttgg actgacaacg gcccggtgat ccctgtggtc tatgattttg     780
gcgacgccca gaaaacagca tcttattact caccctatgg ccagcgggaa ttcactgcgg     840
gatttgttca gttcagggta tttaataacg agagagcagc caacgccttg tgtgctggaa     900
tgagggtcac cggatgtaac actgagcacc actgcattgg tggaggagga tactttccag     960
aggccagtcc ccagcagtgt ggagattttt ctggttttga ttggagtgga tatggaactc    1020
atgttggtta cagcagcagc cgtgagataa ctgaggcagc tgtgcttcta ttctatcgtt    1080
gagagttttg tgggagggaa cccagacctc tcctcccaac catgagatcc caaggatgga    1140
gaacaactta cccagtagct agaatgttaa tggcagaaga gaaaacaata aatcatattg    1200
actcaaaaaa aaaaaaaag                                                 1220
```

<210> SEQ ID NO 7
<211> LENGTH: 2796
<212> TYPE: DNA
<213> ORGANISM: Homo sapiens

<400> SEQUENCE: 7

```
cggctcgagg acaggatga ggcccggcct ctcatttctc ctagcccttc tgttcttcct      60
tggccaagct gcaggggatt tggggatgt gggacctcca attcccagcc ccggcttcag     120
cccttttccca ggtgttgact ccagctccag cttcagctcc agctccaggt cgggctccag    180
ctccagccgc agcttaggca gcggaggttc tgtgtcccag ttgttttcca atttcaccgg    240
ctccgtggat gaccgtggga cctgccagtg tctctgtttcc ctgccagaca ccacctttcc    300
cgtggacaga gtggaacgct tggaattcac agctcatgtt ctttctcaga gtttgagaa     360
agaactttcc aaagtgaggg aatatgtcca attaattagt gtgtatgaaa agaaactgtt    420
aaacctaact gtccgaattg acatcatgga gaaggatacc atttcttaca ctgaactgga    480
cttcgagctg atcaaggtag aagtgaagga gatggaaaaa ctggtcatac agctgaagga    540
gagttttggt ggaagctcag aaattgttga ccagctggag gtggagataa gaaatatgac    600
tctcttggta gagaagcttg agacactaga caaaaacaat gtccttgcca ttcgccgaga    660
aatcgtggct ctgaagacca agctgaaaga gtgtgaggcc tctaaagatc aaaacacccc    720
tgtcgtccac cctcctccca ctccaggagc ctgtggtcat ggtggtgtgg tgaacatcag    780
caaaccgtct gtggttcagc tcaactggag agggttttct tatctatatg gtgcttgggg    840
```

```
tagggattac tctccccagc atccaaacaa aggactgtat tgggtggcgc cattgaatac    900
agatgggaga ctgttggagt attatagact gtacaacaca ctggatgatt tgctattgta    960
tataaatgct cgagagttgc ggatcaccta tggccaaggt agtggtacag cagtttacaa   1020
caacaacatg tacgtcaaca tgtacaacac cgggaatatt gccagagtta acctgaccac   1080
caacacgatt gctgtgactc aaactctccc taatgctgcc tataataacc gcttttcata   1140
tgctaatgtt gcttggcaag atattgactt tgctgtggat gagaatggat tgtgggttat   1200
ttattcaact gaagccagca ctggtaacat ggtgattagt aaactcaatg acaccacact   1260
tcaggtgcta aacacttggt ataccaagca gtataaacca tctgcttcta acgccttcat   1320
ggtatgtggg gttctgtatg ccacccgtac tatgaacacc agaacagaag agatttttta   1380
ctattatgac acaaacacag ggaaagaggg caaactagac attgtaatgc ataagatgca   1440
ggaaaaagtg cagagcatta actataaccc ttttgaccag aaactttatg tctataacga   1500
tggttacctt ctgaattatg atctttctgt cttgcagaag ccccagtaag ctgtttagga   1560
gttagggtga agagaaaat gtttgttgaa aaatagtct ctccactta cttagatatc   1620 tgcagggtg tctaaaagtg tgttcatttt gcagcaatgt ttaggtgcat agttctacca   1680
cactagagat ctaggacatt tgtcttgatt tggtgagttc tcttgggaat catctgcctc   1740
ttcaggcgca ttttgcaata aagtctgtct agggtgggat tgtcagaggt ctaggggcac   1800
tgtgggccta gtgaagccta ctgtgaggag gcttcactag aagccttaaa ttaggaatta   1860
aggaacttaa aactcagtat ggcgtctagg gattctttgt acaggaaata ttgcccaatg   1920
actagtcctc atccatgtag caccactaat tcttccatgc ctggaagaaa cctggggact   1980
tagttaggta gattaatatc tggagctcct cgagggacca aatctccaac ttttttttcc   2040
cctcactaca cctggaatga tgctttgtat gtggcagata agtaaatttg gcatgcttat   2100
atattctaca tctgtaaagt gctgagtttt atggagagag gccttttat gcattaaatt   2160 gtacatggca aataaatccc agaaggatct gtagatgagg cacctgcttt ttcttttctc   2220
tcattgtcca ccttactaaa agtcagtaga atcttctacc tcataacttc cttccaaagg   2280
cagctcagaa gattagaacc agacttacta accaattcca cccccacca acccccttct   2340 actgcctact ttaaaaaat taatagtttt ctatggaact gatctaagat tagaaaaatt   2400
aattttcttt aatttcatta tggactttta tttacatgac tctaagacta taagaaaatc   2460
tgatggcagt gacaaagtgc tagcatttat tgttatctaa taaagacctt ggagcatatg   2520
tgcaacttat gagtgtatca gttgttgcat gtaattttg cctttgttta agcctggaac   2580
ttgtaagaaa atgaaaattt aatttttttt tctaggacga gctatagaaa agctattgag   2640
agtatctagt taatcagtgc agtagttgga aaccttgctg gtgtatgtga tgtgcttctg   2700
tgcttttgaa tgactttatc atctagtctt tgtctgtttt cctttgatg ttcaagtcct   2760 agtctatagg attggcagtt taaatgcttt actccc                             2796
```

<210> SEQ ID NO 8
<211> LENGTH: 2331
<212> TYPE: DNA
<213> ORGANISM: Homo sapiens
<220> FEATURE:
<221> NAME/KEY: misc_feature
<222> LOCATION: (675)..(675)
<223> OTHER INFORMATION: n=a, c, g or t

<400> SEQUENCE: 8

```
tttatcacgg gctcaactgc aacaaaacac ttccttgaca gctccacaaa ctcaggccac    60
```

```
agtgaggaat caacaatatt ccacagcagc ccagatgcaa gtggaacaac accctcatct      120
gcccactcca caacctcagg tcgtggagaa tctacaacct cacgcatcag tccaggctca      180
actgaaataa caacgttacc tggcagtacc acaacaccag gcctcagtga ggcatctacc      240
accttctaca gtagccccag atcaccagac caaacactct cacctgccag catgagaagc      300
tccagcatca gtggagaacc caccagcttg tatagccaag cagagtcaac acacacaaca      360
gcgttccctg ccagcaccac cacctcaggc ctcagtcagg aatcaacaac tttccacagt      420
aagccaggct caactgagac aacactgtcc cctggcagca tcacaacttc atcttttgct      480
caagaattta ccacccctca tagccaacca ggctcagctc tgtcaacagt gtcacctgcc      540
agcaccacag tgccaggcct tagtgaggaa tctaccaccct tctacagcag cccaggctca     600
actgaaacca cagcgttttc tcacagcaac acaatgtcca ttcatagtca acaatctaca      660
cccttccctg acagnccagg cttcactcac acagtgttac ctgccaccct cacaaccaca      720
gacattggtc aggaatcaac agccttccac agcagctcag acgcaactgg aacaacaccc      780
ttacctgccc gctccacagc ctcagacctt gttggagaac ctacaacttt ctacatcagc      840
ccatccccta cttacacaac actctttcct gcgagttcca gcacatcagg cctcactgag      900
gaatctacca ccttccacac cagtccaagc ttcacttcta caattgtgtc tactgaaagc      960
ctggaaacct tagcaccagg gttgtgccag gaaggacaaa tttggaatgg aaaacaatgc     1020
gtctgtcccc aaggctacgt tggttaccag tgcttgtccc ctctggaatc cttccctgta     1080
gaaacccccgg aaaaactcaa cgccactttaa ggtatgacag tgaaagtgac ttacagaaat     1140
ttcacagaaa agatgaatga cgcatcctcc caggaatacc agaacttcag taccctcttc     1200
aagaatcgga tggatgtcgt tttgaagggc gacaatcttc ctcagtatag aggggtgaac     1260
attcggagat tgctcaacgg tagcatcgtg gtcaagaacg atgtcatcct ggaggcagac     1320
tacactttag agtatgagga actgtttgaa aacctggcag agattgtaaa ggccaagatt     1380
atgaatgaaa ctagaacaac tcttcttgat cctgattcct gcagaaaggc catactgtgc     1440
tatagtgaag aggacacttt cgtggattca tcggtgactc cgggctttga cttccaggag     1500
caatgcaccc agaaggctgc cgaaggatat acccagttct actatgtgga tgtcttggat     1560
gggaagctgg cctgtgtgaa caagtgcacc aaaggaacga agtcgcaaat gaactgtaac     1620
ctgggcacat gtcagctgca acgcagtgga ccccgctgc ctgtgcccaa atacgaacac      1680
acactggtac tggggagaga cctgtgaatt caacatcgcc aagagcctcg tgtatgggat     1740
cgtgggggct gtgatggcgg tgctgctgct cgcattgatc atcctaatca tcttattcag     1800
cctatcccag agaaaacggc acagggaaca gtatgatgtg cctcaagagt ggcgaaagga     1860
aggcacccct ggcatcttcc agaagacggc catctgggaa gaccagaatc tgagggagag     1920
cagattcggc cttgagaacg cctacaacaa cttccggccc accctggaga ctgttgactc     1980
tggcacagag ctccacatcc agaggccgga gatggtagca tccactgtgt gagccaacgg     2040
gggcctccca ccctcatcta gctctgttca ggagagctgc aaaacagag cccaccacaa      2100
gcctccgggg cgggtcaaga ggagaccgaa gtcaggccct gaagccggtc ctgctctgag     2160
ctgacagact tggccagtcc cctgcctgtg ctcctgctgg ggaaggctgg gggctgtaag     2220
cctctccatc cgggagcttc cagactccca gaagcctcgg caccctgtc tcctcctggg      2280
tggctcccca ctctggaatt tccctaccaa taaaagcaaa tctgaaagct c               2331
```

<210> SEQ ID NO 9

```
<211> LENGTH: 909
<212> TYPE: DNA
<213> ORGANISM: Homo sapiens

<400> SEQUENCE: 9
gaggaggtgg gcgccaacag acaggcgatt aatgcggctc ttacccaggc aaccaggact    60
acagtataca ttgtggacat tcaggacata gattctgcag ctcgggcccg acctcactcc   120
tacctcgatg cctactttgt cttccccaat gggtcagccc tgaccttga tgagctgagt   180 gtgatgatcc ggaatgatca ggactcgctg acgcagctgc tgcagctggg gctggtggtg   240
ctgggctccc aggagagcca ggagtcagac ctgtcgaaac agctcatcag tgtcatcata   300
ggattgggag tggcttttgct gctggtcctt gtgatcatga ccatggcctt cgtgtgtgtg   360
cggaagagct acaaccggaa gcttcaagct atgaaggctg ccaaggaggc caggaagaca   420
gcagcagggg tgatgccctc agcccctgcc atcccaggga ctaacatgta caacactgag   480
cgagccaacc ccatgctgaa cctccccaac aaagacctgg gcttggagta cctctctccc   540
tccaatgacc tggactctgt cagcgtcaac tccctggacg acaactctgt ggatgtggac   600
aagaacagtc aggaaatcaa ggagcacagg ccaccacaca caccaccaga gccagatcca   660
gagcccctga gcgtggtcct gttaggacgg caggcaggcg caagtggaca gctggagggg   720
ccatcctaca ccaacgctgg cctggacacc acggacctgt gacaggggcc cccactcttc   780
tggacccctt gaagaggccc taccacaccc taactgcacc tgtctccctg gagatgaaaa   840
tatatgacgc tgccctgcct cctgcttttg gccaatcacg gcagacaggg gttggggaaa   900
tattttatt                                                           909

<210> SEQ ID NO 10
<211> LENGTH: 510
<212> TYPE: PRT
<213> ORGANISM: Homo sapiens

<400> SEQUENCE: 10

Met Arg Pro Gly Leu Ser Phe Leu Leu Ala Leu Leu Phe Phe Leu Gly
1               5                   10                  15

Gln Ala Ala Gly Asp Leu Gly Asp Val Gly Pro Ile Pro Ser Pro
            20                  25                  30

Gly Phe Ser Pro Phe Pro Gly Val Asp Ser Ser Ser Phe Ser Ser
            35                  40                  45

Ser Ser Arg Ser Gly Ser Ser Ser Arg Ser Leu Gly Ser Gly Gly
        50                  55                  60

Ser Val Ser Gln Leu Phe Ser Asn Phe Thr Gly Ser Val Asp Asp Arg
65                  70                  75                  80

Gly Thr Cys Gln Cys Ser Val Ser Leu Pro Asp Thr Thr Phe Pro Val
                85                  90                  95

Asp Arg Val Glu Arg Leu Glu Phe Thr Ala His Val Leu Ser Gln Lys
            100                 105                 110

Phe Glu Lys Glu Leu Ser Lys Val Arg Glu Tyr Val Gln Leu Ile Ser
        115                 120                 125

Val Tyr Glu Lys Lys Leu Leu Asn Leu Thr Val Arg Ile Asp Ile Met
    130                 135                 140

Glu Lys Asp Thr Ile Ser Tyr Thr Glu Leu Asp Phe Glu Leu Ile Lys
145                 150                 155                 160

Val Glu Val Lys Glu Met Glu Lys Leu Val Ile Gln Leu Lys Glu Ser
                165                 170                 175
```

-continued

```
Phe Gly Gly Ser Ser Glu Ile Val Asp Gln Leu Glu Val Glu Ile Arg
            180                 185                 190

Asn Met Thr Leu Leu Val Glu Lys Leu Glu Thr Leu Asp Lys Asn Asn
        195                 200                 205

Val Leu Ala Ile Arg Arg Glu Ile Val Ala Leu Lys Thr Lys Leu Lys
    210                 215                 220

Glu Cys Glu Ala Ser Lys Asp Gln Asn Thr Pro Val Val His Pro Pro
225                 230                 235                 240

Pro Thr Pro Gly Ser Cys Gly His Gly Val Val Asn Ile Ser Lys
                245                 250                 255

Pro Ser Val Val Gln Leu Asn Trp Arg Gly Phe Ser Tyr Leu Tyr Gly
            260                 265                 270

Ala Trp Gly Arg Asp Tyr Ser Pro Gln His Pro Asn Lys Gly Leu Tyr
            275                 280                 285

Trp Val Ala Pro Leu Asn Thr Asp Gly Arg Leu Leu Glu Tyr Tyr Arg
    290                 295                 300

Leu Tyr Asn Thr Leu Asp Asp Leu Leu Leu Tyr Ile Asn Ala Arg Glu
305                 310                 315                 320

Leu Arg Ile Thr Tyr Gly Gln Gly Ser Gly Thr Ala Val Tyr Asn Asn
            325                 330                 335

Asn Met Tyr Val Asn Met Tyr Asn Thr Gly Asn Ile Ala Arg Val Asn
            340                 345                 350

Leu Thr Thr Asn Thr Ile Ala Val Thr Gln Thr Leu Pro Asn Ala Ala
            355                 360                 365

Tyr Asn Asn Arg Phe Ser Tyr Ala Asn Val Ala Trp Gln Asp Ile Asp
    370                 375                 380

Phe Ala Val Asp Glu Asn Gly Leu Trp Val Ile Tyr Ser Thr Glu Ala
385                 390                 395                 400

Ser Thr Gly Asn Met Val Ile Ser Lys Leu Asn Asp Thr Thr Leu Gln
            405                 410                 415

Val Leu Asn Thr Trp Tyr Thr Lys Gln Tyr Lys Pro Ser Ala Ser Asn
            420                 425                 430

Ala Phe Met Val Cys Gly Val Leu Tyr Ala Thr Arg Thr Met Asn Thr
    435                 440                 445

Arg Thr Glu Glu Ile Phe Tyr Tyr Tyr Asp Thr Asn Thr Gly Lys Glu
    450                 455                 460

Gly Lys Leu Asp Ile Val Met His Lys Met Gln Glu Lys Val Gln Ser
465                 470                 475                 480

Ile Asn Tyr Asn Pro Phe Asp Gln Lys Leu Tyr Val Tyr Asn Asp Gly
                485                 490                 495

Tyr Leu Leu Asn Tyr Asp Leu Ser Val Leu Gln Lys Pro Gln
            500                 505                 510
```

METHOD OF DIAGNOSING, MONITORING, AND STAGING COLON CANCER

This application claims benefit of U.S. Provisional No. 60/086,266 filed May 21, 1998.

FIELD OF THE INVENTION

This invention relates, in part, to newly developed assays for detecting, diagnosing, monitoring, staging, and prognosticating cancers, particularly colon cancer.

BACKGROUND OF THE INVENTION

Colon cancer is the second most frequently diagnosed malignancy in the United States. Cancer of the gastrointestinal tract, especially colon cancer, is a highly treatable and often a curable disease when localized to the bowel. However, currently colon cancer is the second most common cause of cancer death. Surgery is the primary treatment and results in cure in approximately 50% of patients. Recurrence following surgery is a major problem and often is the ultimate cause of death. The prognosis of colon cancer is clearly related to the degree of penetration of the tumor through the bowel wall and the presence or absence of nodal involvement. These two characteristics form the basis for all staging systems developed for this disease. Bowel obstruction and bowel perforation are indicators of poor prognosis. Elevated pretreatment serum levels of carcinoembryonic antigen (CEA) and carbohydrate antigen 19-9 (CA 19-9) also have negative prognostic significance.

Because of the frequency of the disease (approximately 160,000 new cases of colon cancer per year), the identification of high-risk groups, the demonstrated slow growth of primary lesions, the better survival of early-stage lesions, and the relative simplicity and accuracy of screening tests, screening for colon cancer should be a part of routine care for all adults starting at age 50, especially those with first-degree relatives with colorectal cancer.

Procedures used for detecting, diagnosing, monitoring, staging, and prognosticating colon cancer are of critical importance to the outcome of the patient. For example, patients diagnosed with early colon cancer generally have a much greater five-year survival rate as compared to the survival rate for patients diagnosed with distant metastasized colon cancer. Treatment decisions are usually made in reference to the older Dukes or the Modified Astler-Coller (MAC) classification schema for staging. However, new diagnostic methods which are more sensitive and specific for detecting early colon cancer are clearly needed.

Further, colon cancer patients must be closely monitored following initial therapy and during adjuvant therapy to determine response to therapy and to detect persistent or recurrent disease of metastasis. Thus, there is clearly a need for a colon cancer marker which is more sensitive and specific in detecting colon cancer recurrence.

Another important step in managing colon cancer is to determine the stage of the patient's disease. Stage determination has potential prognostic value and provides criteria for designing optimal therapy. Currently, pathological staging of colon cancer is preferable over clinical staging as pathological staging provides a more accurate prognosis. However, clinical staging would be preferred were the method of clinical staging at least as accurate as pathological staging because it does not depend on an invasive procedure to obtain tissue for pathological evaluation. Staging of colon cancer would be improved by detecting new markers in cells, tissues, or bodily fluids which could differentiate between different stages of invasion.

In the present invention, methods are provided for detecting, diagnosing, monitoring, staging, and prognosticating colon cancers, particularly colon, stomach, and small intestine cancer, via nine (9) Colon Specific Genes (CSGs). The nine CSGs refer, among other things, to native proteins expressed by the genes comprising the polynucleotide sequences of any of SEQ ID NO:1, 2, 3, 4, 5, 6, 7, 8 or 9. In the alternative, what is meant by the nine CSGs as used herein, means the native mRNAs encoded by the genes comprising any of the polynucleotide sequences of SEQ ID NO:1, 2, 3, 4, 5, 6, 7, 8 or 9 or levels of the genes comprising any of the polynucleotide sequences of SEQ ID NO:1, 2, 3, 4, 5, 6, 7, 8 or 9.

Other objects, features, advantages and aspects of the present invention will become apparent to those of skill in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

SUMMARY OF THE INVENTION

Toward these ends, and others, it is an object of the present invention to provide a method for diagnosing the presence of colon cancer in a patient which comprises measuring levels of CSG in a sample of cells, tissue or bodily fluid from the patient and comparing the measured levels of CSG with levels of CSG in preferably the same cells, tissue, or bodily fluid type of a control, wherein an increase in the measured CSG levels in the patient versus levels of CSG in the control is associated with colon cancer.

Another object of the present invention is to provide a method of diagnosing metastatic colon cancer in a patient which comprises measuring CSG levels in a sample of cells, tissue, or bodily fluid from the patient and comparing the measured CSG levels with levels of CSG in preferably the same cells, tissue, or bodily fluid type of a control, wherein an increase in measured CSG levels in the patient versus levels of CSG in the control is associated with a cancer which has metastasized.

Another object of the present invention is to provide a method of staging colon cancer in a patient which comprises identifying a patient having colon cancer, measuring levels of CSG in a sample of cells, tissues, or bodily fluid obtained from the patient, and comparing the measured CSG levels with levels of CSG in preferably the same cells, tissue or bodily fluid type of a control. An increase in measured CSG levels in the patient versus CSG levels in the control can be associated with a cancer which is progressing while a decrease or equivalent level of CSG measured in the patient versus the control can be associated with a cancer which is regressing or in remission.

Another object of the present invention is to provide a method of monitoring colon cancer in a patient for the onset of metastasis. The method comprises identifying a patient having colon cancer that is not known to have metastasized, periodically measuring levels of CSG in a sample of cells, tissues, or bodily fluid obtained from the patient, and comparing the measured CSG levels with levels of CSG in preferably the same cells, tissue, or bodily fluid type of a control, wherein an increase in measured CSG levels versus control CSG levels is associated with a cancer which has metastasized.

Yet another object of the present invention is to provide a method of monitoring the change in stage of colon cancer in a patient which comprises identifying a patient having colon cancer, periodically measuring levels of CSG in a sample of cells, tissue, or bodily fluid obtained from the patient, and comparing the measured CSG levels with levels of CSG in preferably the same cells, tissues, or bodily fluid type of a control wherein an increase in measured CSG levels versus the control CSG levels is associated with a cancer which is progressing and a decrease in the measured CSG levels versus the control CSG levels is associated with a cancer which is regressing or in remission.

Other objects, features, advantages and aspects of the present invention will become apparent to those of skill in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

DESCRIPTION OF THE INVENTION

The present invention relates to diagnostic assays and methods, both quantitative and qualitative for detecting, diagnosing, monitoring, staging, and prognosticating cancers by comparing levels of CSG with those of CSG in a normal human control. What is meant by "levels of CSG" as used herein, means levels of the native protein expressed by the genes comprising the polynucleotide sequence of any of SEQ ID NO: 1, 2, 3, 4, 5, 6, 7, 8 or 9. In the alternative, what is meant by "levels of CSG" as used herein, means levels of the native mRNA encoded by any of the genes comprising any of the polynucleotide sequences of SEQ ID NO: 1, 2, 3, 4, 5, 6, 7, 8 or 9 or levels of the gene comprising any of the polynucleotide sequence of SEQ ID NO: 1, 2, 3, 4, 5, 6, 7, 8 or 9. Such levels are preferably measured in at least one of, cells, tissues and/or bodily fluids, including determination of normal and abnormal levels. Thus, for instance, a diagnostic assay in accordance with the invention for diagnosing over-expression of any one of the CSG proteins compared to normal control bodily fluids, cells, or tissue samples may be used to diagnose the presence of cancers, including colon cancer. Any of the nine CSGs may be measured alone in the methods of the invention, or all together or any combination of the nine.

By "control" it is meant a human patient without cancer and/or non cancerous samples from the patient, also referred to herein as a normal human control; in the methods for diagnosing or monitoring for metastasis, control may also include samples from a human patient that is determined by reliable methods to have colon cancer which has not metastasized.

All the methods of the present invention may optionally include measuring the levels of other cancer markers as well as CSG. Other cancer markers, in addition to CSG, useful in the present invention will depend on the cancer being tested and are known to those of skill in the art.

Diagnostic Assays

The present invention provides methods for diagnosing the presence of colon cancer by analyzing for changes in levels of CSG in cells, tissues or bodily fluids compared with levels of CSG in cells, tissues or bodily fluids of preferably the same type from a normal human control, wherein an increase in levels of CSG in the patient versus the normal human control is associated with the presence of colon cancer. Without limiting the instant invention, typically, for a quantitative diagnostic assay a positive result indicating the patient being rested has cancer is one in which cells, tissues, or bodily fluid levels of the cancer marker, such as CSG, are at least two times higher, and most preferably are at least five times higher, than in preferably the same cells, tissues, or bodily fluid of a normal human control.

The present invention also provides a method of diagnosing metastatic colon cancer in a patient having colon cancer which has not yet metastasized for the onset of metastasis. In the method of the present invention, a human cancer patient suspected of having colon cancer which may have metastasized (but which was not previously known to have metastasized) is identified. This is accomplished by a variety of means known to those of skill in the art. For example, in the case of colon cancer, patients are typically diagnosed with colon cancer following traditional detection methods.

In the present invention, determining the presence of CSG level in cells, tissues, or bodily fluid, is particularly useful for discriminating between colon cancer which has not metastasized and colon cancer which has metastasized. Existing techniques have difficulty discriminating between colon cancer which has metastasized and colon cancer which has not metastasized and proper treatment selection is often dependent upon such knowledge.

In the present invention, the cancer marker levels measured in such cells, tissues, or bodily fluid is CSG, and are compared with levels of CSG in preferably the same cells, tissue, or bodily fluid type of a normal human control. That is, if the cancer marker being observed is just CSG in serum, this level is preferably compared with the level of CSG in serum of a normal human patient. An increase in the CSG in the patient versus the normal human control is associated with colon cancer which has metastasized.

Without limiting the instant invention, typically, for a quantitative diagnostic assay a positive result indicating the cancer in the patient being tested or monitored has metastasized is one in which cells, tissues, or bodily fluid levels of the cancer marker, such as CSG, are at least two times higher, and most preferable are at least five times higher, than in preferably the same cells, tissues, or bodily fluid of a normal patient.

Normal human control as used herein includes a human patient without cancer and/or non cancerous samples from the patient; in the methods for diagnosing or monitoring for metastasis, normal human control may also include samples from a human patient that is determined by reliable methods to have colon cancer which has not metastasized.

Staging

The invention also provides a method of staging colon cancer in a human patient.

The method comprises identifying a human patient having such cancer; analyzing a sample of cells, tissues, or bodily fluid from such patient for CSG. Then, the method compares CSG levels in such cells, tissues, or bodily fluid with levels of CSG in preferably the same cells, tissues, or bodily fluid type of a normal human control sample, wherein an increase in CSG levels in the patient versus the normal human control is associated with a cancer which is progressing and a decrease in the levels of CSG is associated with a cancer which is regressing or in remission.

Monitoring

Further provided is a method of monitoring colon cancer in a human having such cancer for the onset of metastasis. The method comprises identifying a human patient having such cancer that is not known to have metastasized; periodically analyzing a sample of cells, tissues, or bodily fluid from such patient for CSG; comparing the CSG levels in such cells, tissue, or bodily fluid with levels of CSG in preferably the same cells, tissues, or bodily fluid type of a normal human control sample, wherein an increase in CSG levels in the patient versus the normal human control is associated with a cancer which has metastasized.

Further provided by this inventions is a method of monitoring the change in stage of colon cancer in a human having such cancer. The method comprises identifying a human patient having such cancer; periodically analyzing a sample of cells, tissues, or bodily fluid from such patient for CSG; comparing the CSG levels in such cells, tissue, or bodily fluid with levels of CSG in preferably the same cells, tissues, or bodily fluid type of a normal human control sample, wherein an increase in CSG levels in the patient versus the normal human control is associated with a cancer which is progressing in stage and a decrease in the levels of CSG is associated with a cancer which is regressing in stage or in remission.

Monitoring such patient for onset of metastasis is periodic and preferably done on a quarterly basis. However, this may be more or less frequent depending on the cancer, the particular patient, and the stage of the cancer.

Assay Techniques

Assay techniques that can be used to determine levels of gene expression, such as CSG of the present invention, in a sample derived from a host are well-known to those of skill in the art. Such assay methods include radioimmunoassays, reverse transcriptase PCR (RT-PCR) assays, immunohistochemistry assays, in situ hybridization assays, competitive-binding assays, Western Blot analyses and ELISA assays. Among these, ELISAs are frequently preferred to diagnose a gene's expressed protein in biological fluids. An ELISA assay initially comprises preparing an antibody, if not readily available from a commercial source, specific to CSG, preferably a monoclonal antibody. In addition a reporter antibody generally is prepared which binds specifically to CSG. The reporter antibody is attached to a detectable reagent such as radioactive, fluorescent or enzymatic reagent, for example horseradish peroxidase enzyme or alkaline phosphatase.

To carry out the ELISA, antibody specific to CSG is incubated on a solid support, e.g., a polystyrene dish, that binds the antibody. Any free protein binding sites on the dish are then covered by incubating with a non-specific protein such as bovine serum albumin. Next, the sample to be analyzed is incubated in the dish, during which time CSG binds to the specific antibody attached to the polystyrene dish. Unbound sample is washed out with buffer. A reporter antibody specifically directed to CSG and linked to horseradish peroxidase is placed in the dish resulting in binding of the reporter antibody to any monoclonal antibody bound to CSG. Unattached reporter antibody is then washed out. Reagents for peroxidase activity, including a calorimetric substrate are then added to the dish. Immobilized peroxidase, linked to CSG antibodies, produces a colored reaction product. The amount of color developed in a given time period is proportional to the amount of CSG protein present in the sample. Quantitative results typically are obtained by reference to a standard curve.

A competition assay may be employed wherein antibodies specific to CSG attached to a solid support and labeled CSG and a sample derived from the host are passed over the solid support and the amount of label detected attached to the solid support can be correlated to a quantity of CSG in the sample. Nucleic acid methods may be used to detect CSG mRNA as a marker for colon cancer. Polymerase chain reaction (PCR) and other nucleic acid methods, such as ligase chain reaction (LCR) and nucleic acid sequence based amplification (NASABA), can be used to detect malignant cells for diagnosis and monitoring of various malignancies. For example, reverse-transcriptase PCR (RT-PCR) is a powerful technique which can be used to detect the presence of a specific mRNA population in a complex mixture of thousands of other mRNA species. In RT-PCR, an mRNA species is first reverse transcribed to complementary DNA (cDNA) with use of the enzyme reverse transcriptase; the cDNA is then amplified as in a standard PCR reaction. RT-PCR can thus reveal by amplification the presence of a single species of mRNA. Accordingly, if the mRNA is highly specific for the cell that produces it, RT-PCR can be used to identify the presence of a specific type of cell.

Hybridization to clones or oligonucleotides arrayed on a solid support (i.e., gridding) can be used to both detect the expression of and quantitate the level of expression of that gene. In this approach, a cDNA encoding the CSG gene is fixed to a substrate. The substrate may be of any suitable type including but not limited to glass, nitrocellulose, nylon or plastic. At least a portion of the DNA encoding the CSG gene is attached to the substrate and then incubated with the analyte, which may be RNA or a complementary DNA (cDNA) copy of the RNA, isolated from the tissue of interest.

Hybridization between the substrate bound DNA and the analyte can be detected and quantitated by several means including but not limited to radioactive labeling or fluorescence labeling of the analyte or a secondary molecule designed to detect the hybrid. Quantitation of the level of gene expression can be done by comparison of the intensity of the signal from the analyte compared with that determined from known standards. The standards can be obtained by in vitro transcription of the target gene, quantitating the yield, and then using that material to generate a standard curve.

The above tests can be carried out on samples derived from a variety of patients' cells, bodily fluids and/or tissue extracts (homogenates or solubilized tissue) such as from tissue biopsy and autopsy material. Bodily fluids useful in the present invention include blood, urine, saliva, or any other bodily secretion or derivative thereof. Blood can include whole blood, plasma, serum, or any derivative of blood.

EXAMPLES

The present invention is further described by the following examples. These examples are provided solely to illustrate the invention by reference to specific embodiments. These exemplifications, while illustrating certain specific aspects of the invention, do not portray the limitations or circumscribe the scope of the disclosed invention.

Example 1

CSGs

Searches were carried out and CSGs identified using the following Search Tools as part of the LIFESEQ® database available from Incyte Pharmaceuticals, Palo Alto, Calif.:

1. Library Comparison (compares one library to one other library) allows the identification of clones expressed in tumor and absent or expressed at a lower level in normal tissue.

2. Subsetting is similar to library comparison but allows the identification of clones expressed in a pool of libraries and absent or expressed at a lower level in a second pool of libraries.

3. Transcript Imaging lists all of the clones in a single library or a pool of libraries based on abundance. Individual clones can then be examined using Electronic Northerns to determine the tissue sources of their component ESTs.

4. Protein Function: Incyte has identified subsets of ESTs with a potential protein function based on homologies to known proteins. Some examples in this database include Transcription Factors and Proteases. We identified some leads by searching in this database for clones whose component ESTs showed disease specificity.

Electronic subtractions, transcript imaging and protein function searches were used to identify clones, whose component ESTs were exclusively or more frequently found in libraries from specific tumors. Individual candidate clones were examined in detail by checking where each EST originated.

TABLE 1

CSGs

| SEQ ID NO: | Clone ID # | Gene ID # | |
|---|---|---|---|
| 1 | 238330 | 242807 | Transcript Imaging |
| 2 | 1285234 | 239588 | Subsetting |
| 3 | 1341701 | 29634 | Transcript Imaging |
| 4 | 816257 | 233421 | Subsetting |
| 5 | 775133 | 245080 | Subsetting |
| 6 | 1335450 | 245811 | Subsetting |
| 7 | 2348122 | 233711 | Transcript Imaging |
| 8 | 3228674 | 230273 | Subsetting |
| 9 | 1632174 | 229022 | Transcript Imaging |

The following example was carried out using standard techniques, which are well known and routine to those of skill in the art, except where otherwise described in detail. Routine molecular biology techniques of the following example can be carried out as described in standard laboratory manuals, such as Sambrook et al., MOLECULAR CLONING: A LABORATORY MANUAL, 2nd Ed.; Cold Spring Harbor Laboratory Press, Cold Spring Harbor, N.Y. (1989).

Example 2

Relative Quantitation of CSG Gene Expression

Real-Time quantitative PCR with fluorescent Taqman probes is a quantitation detection system utilizing the 5'-3' nuclease activity of Taq DNA polymerase. The method uses an internal fluorescent oligonucleotide probe (Taqman) labeled with a 5' reporter dye and a downstream, 3' quencher dye. During PCR, the 5'-3' nuclease activity of Taq DNA polymerase releases the reporter, whose fluorescence can then be detected by the laser detector of the Model 7700 Sequence Detection System (PE Applied Biosystems, Foster City, Calif., USA).

Amplification of an endogenous control is used to standardize the amount of sample RNA added to the reaction and normalize for Reverse Transcriptase (RT) efficiency. Either cyclophilin, glyceraldehyde-3-phosphate dehydrogenase (GAPDH) or 18S ribosomal RNA (rRNA) is used as this endogenous control. To calculate relative quantitation between all the samples studied, the target RNA levels for one sample are used as the basis for comparative results (calibrator). Quantitation relative to the "calibrator" can be obtained using the standard curve method or the comparative method (User Bulletin #2: ABI PRISM 7700 Sequence Detection System).

To evaluate the tissue distribution, and the level of CSGs in normal and tumor tissue, total RNA was extracted from normal tissues, tumor tissues, and from tumors and the corresponding matched normal tissues. Subsequently, first strand cDNA was prepared with reverse transcriptase and the polymerase chain reaction was done using primers and Taqman probe specific to the CSG. The results were analyzed using the ABI PRISM 7700 Sequence Detector. The absolute numbers are relative levels of expression of the CSG compared to the calibrator.

Comparative Examples

Similar mRNA expression analysis for genes coding for the diagnostic markers PSA (Prostate Specific Antigen) and PLA2 (Phospholipase A2) was performed for comparison. PSA is currently the only cancer screening marker available in clinical laboratories. When the panel of normal pooled tissues was analyzed, PSA was expressed at very high levels in prostate, with a very low expression in breast and testis. After analysis of more than 55 matching samples from 14 different tissues, the data corroborated the tissue specificity seen with normal tissue samples. PSA expression was compared in cancer and normal adjacent tissue for 12 matching samples of prostate tissue. The relative levels of PSA were higher in 10 cancer samples (83%). Clinical data recently obtained support the utilization of PLA2 as a staging marker for late stages of prostate cancer. mRNA expression data described herein showed overexpression of the mRNA in 8 out of the 12 prostate matching samples analyzed (66%). PLA2 had high levels of mRNA expression in small intestine, prostate, liver, and pancreas.

Measurement of SEQ ID NO:3; Clone ID 1341701; Gene ID 29634 (Cln106)

Absolute numbers are depicted in Table 2 as relative levels of expression of Cln106 (SEQ ID NO:3) in 12 normal different tissues. All the values are compared to normal testis (calibrator). These RNA samples are commercially available pools, originated by pooling samples of a particular tissue from different individuals.

TABLE 2

Relative levels of Cln106 Expression in Pooled Samples

| Tissue | NORMAL |
|---|---|
| Colon-Ascending | 110 |
| Endometrium | 0 |
| Kidney | 0 |
| Liver | 0 |
| Ovary | 0 |
| Pancreas | 0 |
| Prostate | 16 |
| Small Intestine | 0 |
| Spleen | 0 |
| Stomach | 0 |
| Testis | 1 |
| Uterus | 0 |

The relative levels of expression in Table 2 show for the CSG Cln106 (SEQ ID NO:3), mRNA expression is more than 6 fold higher in the pool of normal ascending colon (110) compared with prostate (16). Testis, the calibrator, with a relative expression level of 1, is the only other tissue expressing the mRNA for Cln106 (SEQ ID NO:3). These results demonstrate that mRNA expression of this CSG is highly specific for colon.

The absolute numbers in Table 2 were obtained analyzing pools of samples of a particular tissue from different individuals. They can not be compared to the absolute numbers originated from RNA obtained from tissue samples of a single individual in Table 3.

The absolute numbers in Table 3 are relative levels of expression of Cln106 (SEQ ID NO:3) in 57 pairs of matching samples. All the values are compared to normal testis (calibrator). A matching pair is formed by mRNA from the cancer sample for a particular tissue and mRNA from the normal adjacent sample for that same tissue from the same individual.

TABLE 3

Relative levels of Cln106 Expression in Individual Samples

| Sample ID | Tissue | Cancer | Matching Normal Adjacent |
|---|---|---|---|
| Sto AC93 | Stomach 1 | 4 | 96 |
| Sto AC99 | Stomach 2 | 0.4 | 0.5 |
| Sml 21XA | Small Intestine 1 | 0 | 0 |
| Sml H89 | Small Intestine 2 | 0.93 | 1.28 |
| Cln B56 | Colon-Cecum (A) 1 | 317 | 101 |
| Cln AS45 | Colon-Ascending (A) 2 | 316.3 | 146.5 |
| Cln CM67 | Colon-Cecum (B) 3 | 481.0 | 217.5 |
| Cln AS67 | Colon-Ascending (B) 4 | 858.1 | 220.6 |
| Cln AS43 | Colon-Ascending (C) 5 | 1370 | 98 |
| Cln AS46 | Colon-Ascending (C) 6 | 3051 | 375 |
| Cln AS98 | Colon-Ascending (C) 7 | 26 | 42 |
| Cln AS89 | Colon-Ascending (D) 8 | 524.6 | 11.0 |
| Cln TX01 | Colon-Transverse (B) 9 | 2886.3 | 1992.0 |
| Cln TX89 | Colon-Transverse (B) 10 | 146.0 | 35.9 |
| Cln TX67 | Colon-Transverse (C) 11 | 2.9 | 421.7 |
| Cln MT38 | Colon-Splenic Flexture (M) 12 | 1681 | 187 |
| Cln SG89 | Colon-Sigmoid (B) 13 | 1063.8 | 31.1 |
| Cln SG67 | Colon-Sigmoid (C) 14 | 8.5 | 9.4 |
| Cln SG33 | Colon-Sigmoid (C) 15 | 264 | 549 |
| Cln SG45 | Colon-Sigmoid (D) 16 | 580.0 | 114.6 |
| Cln B34 | Colon-Rectosigmoid (A) 17 | 97 | 244 |
| Cln CXGA | Colon-Rectum (A) 18 | 45.1 | 273.4 |
| Cln RC67 | Colon-Rectum (B) 19 | 2.7 | 20.0 |
| Cln C9XR | Colon-Rectosigmoid (C) 20 | 609 | 460 |
| Cln RS45 | Colon-Rectosigmoid (C) 21 | 472.8 | 144.0 |
| Cln RC01 | Colon-Rectum (C) 22 | 568 | 129 |
| Cln RC89 | Colon-Rectum (D) 23 | 4.6 | 322.91 |
| Bld 46XK | Bladder 1 | 0.2 | 0 |
| Bld 66X | Bladder 2 | 1 | 1 |
| Bld 32XK | Bladder 3 | 0.0 | 0.0 |
| Kid 126XD | Kidney 1 | 0 | 0 |
| Kid 12XD | Kidney 2 | 0 | 0 |
| Kid 5XD | Kidney 3 | 0.0 | 1.0 |
| Kid 6XD | Kidney 4 | 0.0 | 0.0 |
| Kid 106XD | Kidney 5 | 0.4 | 0.0 |
| Liv 42X | Liver 1 | 0.0 | 0.0 |
| Liv 15XA | Liver 2 | 0.0 | 0.0 |
| Liv 94XA | Liver 3 | 0.0 | 0.0 |
| Lng AC69 | Lung 1 | 2 | 0 |
| Lng BR94 | Lung 2 | 0 | 0 |
| Lng 47XQ | Lung 3 | 0 | 0 |
| Mam 59X | Mammary Gland 1 | 0 | 0 |
| Mam B011X | Mammary Gland 2 | 0 | 0 |
| Mam A06X | Mammary Gland 3 | 0 | 0 |
| Ovr 103X | Ovary 1 | 0.04 | 2.08 |
| Ovr 130X | Ovary 2 | 0.1 | 2.76 |
| Pan 71XL | Pancreas 1 | 4.08 | 0.1 |
| Pan 82XP | Pancreas 2 | 0 | 0 |
| Pro 12B | Prostate 1 | 0.3 | 0 |
| Pro 23B | Prostate 2 | 3 | 4 |
| Pro 13XB | Prostate 3 | 2 | 7 |
| Pro 34B | Prostate 4 | 0.54 | 4.01 |
| Pro 20XB | Prostate 5 | 4.8 | 4.3 |
| Pro 65XB | Prostate 6 | 0.7 | 1.3 |
| Tst 39X | Testis 1 | 2.78 | 0 |
| End 8XA | Endometrium 1 | 0 | 0.2 |
| Utr 85XU | Uterus 1 | 1.26 | 0 |

0 = Negative

When matching samples were analyzed, the higher levels of expression were in the colon, showing a high degree of tissue specificity for this tissue. These results confirm the tissue specificity results obtained with the panel of normal pooled samples (Table 2). Furthermore, the level of mRNA expression in cancer samples and the isogenic normal adjacent tissue from the same individual were compared. This comparison provides an indication of specificity for the cancer stage (e.g. higher levels of mRNA expression in the cancer sample compared to the normal adjacent). Table 3 shows overexpression of Cln106 (SEQ ID NO:3) in 15 colon cancer tissues compared with their respective normal adjacent (colon samples #1, 2, 3, 4, 5, 6, 8, 9, 10, 12, 13, 16, 20, 21, and 22). There is overexpression in the cancer tissue for 65% of the colon matching samples tested (total of 23 colon matching samples). The matching sample Pan 71XL is a secondary cancer in pancreas, the primary cancer in that individual was a duodenal cancer.

Altogether, the high level of tissue specificity, plus the mRNA overexpression in 65% of the colon matching samples tested are demonstrative of CSG Cln106 (SEQ ID NO:3) being a diagnostic marker for colon cancer.

Measurement of SEQ ID NO:4; Clone ID 816257; Gene ID 406452 (Cln107)

Absolute numbers as depicted in Table 4 are relative levels of expression of CSG Cln107 (SEQ ID NO:4) in 12 normal different tissues. All the values are compared to normal small intestine (calibrator). These RNA samples are commercially available pools, originated by pooling samples of a particular tissue from different individuals.

TABLE 4

Relative levels of Cln107 Expression in Pooled Samples

| Tissue | NORMAL |
|---|---|
| Colon-Ascending | 3.2 |
| Endometrium | 0 |
| Kidney | 0.2 |
| Liver | 0 |
| Ovary | 0 |
| Pancreas | 0 |
| Prostate | 0.1 |
| Small Intestine | 1 |
| Spleen | 0 |
| Stomach | 0.3 |
| Testis | 0 |
| Uterus | 0 |

The relative levels of expression in Table 4 show that mRNA expression of the CSG Cln107 (SEQ ID NO:4) is more than 10 fold higher in the pool of normal ascending colon (3.2), five fold higher in small intestine (1), and 1.5 fold higher in stomach (0.3), compared with the next higher expresser (0.2 for kidney). Seven of the pooled tissues samples analyzed were negative and prostate showed a relative expression of 0.1 for Cln107 (SEQ ID NO:4). These results demonstrate that Cln107 mRNA expression is highly specific for colon, small intestine, and in a lower degree for stomach.

The absolute numbers in Table 4 were obtained analyzing pools of samples of a particular tissue from different individuals. They can not be compared to the absolute numbers originated from RNA obtained from tissue samples of a single individual in Table 5.

The absolute numbers in Table 5 are relative levels of expression of Cln107 (SEQ ID NO:4) in 57 pairs of matching samples. All the values are compared to normal small intestine (calibrator). A matching pair is formed by mRNA from the cancer sample for a particular tissue and mRNA from the normal adjacent sample for that same tissue from the same individual.

TABLE 5

Relative levels of Cln107 Expression in Individual Samples

| Sample ID | Tissue | Cancer | Matching Normal Adjacent |
|---|---|---|---|
| Sto AC93 | Stomach 1 | 8.9 | 13.4 |
| Sto AC99 | Stomach 2 | 6.0 | 0.9 |
| Sml 21XA | Small Intestine 1 | 1.07 | 1.42 |
| Sml H89 | Small Intestine 2 | 0.97 | 4.13 |
| Cln B56 | Colon-Cecum (A) 1 | 2 | 16 |
| Cln AS45 | Colon-Ascending (A) 2 | 0.7 | 2.1 |
| Cln CM67 | Colon-Cecum (B) 3 | 1.6 | 2.1 |
| Cln AS67 | Colon-Ascending (B) 4 | 1.2 | 6.2 |
| Cln AS43 | Colon-Ascending (C) 5 | 13.5 | 0.5 |
| Cln AS46 | Colon-Ascending (C) 6 | 9.7 | 23.6 |
| Cln AS98 | Colon-Ascending (C) 7 | 28.1 | 1.4 |
| Cln AS89 | Colon-Ascending (D) 8 | 0.9 | 3.1 |
| Cln TX01 | Colon-Transverse (B) 9 | 3.0 | 10.6 |
| Cln TX89 | Colon-Transverse (B) 10 | 4.5 | 0.6 |
| Cln TX67 | Colon-Transverse (C) 11 | 3.6 | 3.4 |
| Cln MT38 | Colon-Splenic Flexture (M) 12 | 4.0 | 2.6 |
| Cln SG89 | Colon-Sigmoid (B) 13 | 4.7 | 0.9 |
| Cln SG67 | Colon-Sigmoid (C) 14 | 1.0 | 1.3 |
| Cln SG33 | Colon-Sigmoid (C) 15 | 14.2 | 7.6 |
| Cln SG45 | Colon-Sigmoid (D) 16 | 4.8 | 6.0 |
| Cln B34 | Colon-Rectosigmoid (A) 17 | 3 | 2 |
| Cln CXGA | Colon-Rectum (A) 18 | 4.4 | 1.9 |
| Cln RC67 | Colon-Rectum (B) 19 | 0.1 | 0.4 |
| Cln C9XR | Colon-Rectosigmoid (C) 20 | 5 | 3 |
| Cln RS45 | Colon-Rectosigmoid (C) 21 | 11.4 | 4.6 |
| Cln RC01 | Colon-Rectum (C) 22 | 1.8 | 2.3 |
| Cln RC89 | Colon-Rectum (D) 23 | 0.1 | 5.35 |
| Bld 46XK | Bladder 1 | 0.2 | 0 |
| Bld 66X | Bladder 2 | 1 | 1 |
| Bld 32XK | Bladder 3 | 0.1 | 0.1 |
| Kid 126XD | Kidney 1 | 0 | 0.02 |
| Kid 12XD | Kidney 2 | 0.1 | 0.2 |
| Kid 5XD | Kidney 3 | 0.3 | 0.0 |
| Kid 6XD | Kidney 4 | 0.1 | 0.1 |
| Kid 106XD | Kidney 5 | 0.0 | 0.1 |
| Liv 42X | Liver 1 | 7.9 | 0.002 |
| Liv 15XA | Liver 2 | 0.0 | 0.0 |
| Liv 94XA | Liver 3 | 0.0 | 0.0 |
| Lng AC69 | Lung 1 | 1.6 | 0.2 |
| Lng BR94 | Lung 2 | 0.4 | 0 |
| Lng 47XQ | Lung 3 | 0.78 | 0.2 |
| Mam 59X | Mammary Gland 1 | 0.05 | 0.3 |
| Mam B011X | Mammary Gland 2 | 0.01 | 0.004 |
| Mam A06X | Mammary Gland 3 | 0.22 | 0 |
| Ovr 103X | Ovary 1 | 0.01 | 0.01 |
| Ovr 130X | Ovary 2 | 0.09 | 0.1 |
| Pan 71XL | Pancreas 1 | 2.51 | 2.81 |
| Pan 82XP | Pancreas 2 | 0 | 0.62 |
| Pro 12B | Prostate 1 | 0.3 | 0.1 |

TABLE 5-continued

Relative levels of Cln107 Expression in Individual Samples

| Sample ID | Tissue | Cancer | Matching Normal Adjacent |
|---|---|---|---|
| Pro 23B | Prostate 2 | 0.3 | 0.2 |
| Pro 13XB | Prostate 3 | 0 | 0 |
| Pro 34B | Prostate 4 | 0.04 | 0.22 |
| Pro 20XB | Prostate 5 | 0.4 | 0.1 |
| Pro 65XB | Prostate 6 | 0.0 | 0.1 |
| Tst 39X | Testis 1 | 0.02 | 0.01 |
| End 8XA | Endometrium 1 | 0.01 | 0.5 |
| Utr 85XU | Uterus 1 | 0.03 | 0 |

0 = Negative

When matching samples were analyzed, the higher levels of expression were in colon, stomach, and small intestine, showing a high degree of tissue specificity for colon tissues. These results confirm the tissue specificity results obtained with normal pooled samples (Table 4). Furthermore, the level of mRNA expression in cancer samples and the isogenic normal adjacent tissue from the same individual were compared. This comparison provides an indication of specificity for the cancer stage (e.g. higher levels of mRNA expression in the cancer sample compared to the normal adjacent). Table 5 shows overexpression of Cln107 (SEQ ID NO:4) in 11 colon cancer tissues compared with their respective normal adjacent (colon samples #5, 7, 10, 11, 12, 13, 15, 17, 18, 20, and 21). There is overexpression in the cancer tissue for 48% of the colon matching samples tested (total of 23 colon matching samples). The matching sample Pan 71XL is a secondary cancer in pancreas, the primary cancer in that individual was a duodenal cancer.

Altogether, the high level of tissue specificity, plus the mRNA overexpression in almost half of the colon, stomach, and small intestine matching samples tested are demonstrative of CSG Cln107 (SEQ ID NO:4) being a diagnostic marker for colon cancer.

Measurement of SEQ ID NO:5; Clone ID 775133; Gene ID 24508 (Cln108)

The absolute numbers shown in Table 6 are relative levels of expression of CSG Cln108 (SEQ ID NO:5) in 12 normal different tissues. All the values are compared to normal small intestine (calibrator). These RNA samples are commercially available pools, originated by pooling samples of a particular tissue from different individuals.

TABLE 6

Relative levels of Cln108 Expression in Pooled Samples

| Tissue | NORMAL |
|---|---|
| Colon-Ascending | 2846.5 |
| Endometrium | 1 |
| Kidney | 5.5 |
| Liver | 18.7 |
| Ovary | 3.4 |
| Pancreas | 198.1 |
| Prostate | 1024 |
| Small Intestine | 810.8 |
| Spleen | 32.2 |
| Stomach | 9981.2 |
| Testis | 0 |
| Uterus | 294.1 |

The relative levels of expression in Table 6 show that mRNA expression of CSG Cln108 (SEQ ID NO:5) is more than 10 fold higher in the pool of normal ascending colon (2846.5) and almost ten fold higher in stomach (9981.2), compared to the expression level in any other tissue analyzed. These results demonstrate that mRNA expression of this CSG is also highly specific for colon and stomach.

The absolute numbers in Table 6 were obtained analyzing pools of samples of a particular tissue from different individuals. They can not be compared to the absolute numbers originated from RNA obtained from tissue samples of a single individual in Table 7.

The absolute numbers depicted in Table 7 are relative levels of expression of Cln108 (SEQ ID NO:5) in 57 pairs of matching samples. All the values are compared to normal small intestine (calibrator). A matching pair is formed by mRNA from the cancer sample for a particular tissue and mRNA from the normal adjacent sample for that same tissue from the same individual.

TABLE 7

Relative levels of Cln108 Expression in Individual Samples

| Sample ID | Tissue | Cancer | Matching Normal Adjacent |
|---|---|---|---|
| Sto AC93 | Stomach 1 | 28696 | 34842 |
| Sto AC99 | Stomach 2 | 21523 | 30862 |
| Sml 21XA | Small Intestine 1 | 2944 | 964.4 |
| Sml H89 | Small Intestine 2 | 244.5 | 3513.2 |
| Cln B56 | Colon-Cecum (A) 1 | 27242 | 24637 |
| Cln AS45 | Colon-Ascending (A) 2 | 5827.0 | 8771.0 |
| Cln CM67 | Colon-Cecum (B) 3 | 4251.0 | 4684.0 |
| Cln AS67 | Colon-Ascending (B) 4 | 564.0 | 1949.0 |
| Cln AS43 | Colon-Ascending (C) 5 | 50310 | 10949 |
| Cln AS46 | Colon-Ascending (C) 6 | 246044 | 120073 |
| Cln AS98 | Colon-Ascending (C) 7 | 40442 | 17482 |
| Cln AS89 | Colon-Ascending (D) 8 | 5730.0 | 1581.0 |
| Cln TX01 | Colon-Transverse (B) 9 | 22281.0 | 114784.0 |
| Cln TX89 | Colon-Transverse (B) 10 | 11026.0 | 1639.0 |
| Cln TX67 | Colon-Transverse (C) 11 | 17004.0 | 11654.0 |
| Cln MT38 | Colon-Splenic Flexture (M) 12 | 77589 | 31620 |
| Cln SG89 | Colon-Sigmoid (B) 13 | 140339.0 | 49617.0 |
| Cln SG67 | Colon-Sigmoid (C) 14 | 4951.0 | 7905.0 |
| Cln SG33 | Colon-Sigmoid (C) 15 | 60875 | 120490 |
| Cln SG45 | Colon-Sigmoid (D) 16 | 30437.0 | 47267.0 |
| Cln B34 | Colon-Rectosigmoid (A) 17 | 5848 | 5861 |
| Cln CXGA | Colon-Rectum (A) 18 | 13877.0 | 9787.0 |
| Cln RC67 | Colon-Rectum (B) 19 | 1703.0 | 26589.0 |
| Cln C9XR | Colon-Rectosigmoid (C) 20 | 2458 | 19071 |
| Cln RS45 | Colon-Rectosigmoid (C) 21 | 95523 | 61939 |
| Cln RC01 | Colon-Rectum (C) 22 | 98891.0 | 80047.0 |
| Cln RC89 | Colon-Rectum (D) 23 | 17.0 | 1775 |
| Bld 46XK | Bladder 1 | 0 | 8 |
| Bld 66X | Bladder 2 | 397 | 44 |
| Bld 32XK | Bladder 3 | 0.0 | 16.0 |
| Kid 126XD | Kidney 1 | 32 | 22 |
| Kid 12XD | Kidney 2 | 6 | 0 |
| Kid 106XD | Kidney 3 | 4.0 | 33.0 |
| Liv 42X | Liver 1 | 4783 | 0 |
| Liv 15XA | Liver 2 | 4.0 | 10.0 |
| Liv 94XA | Liver 3 | 159.0 | 21.0 |
| Lng AC69 | Lung 1 | 222 | 295 |
| Lng BR94 | Lung 2 | 112 | 0 |
| Lng 47XQ | Lung 3 | 30 | 69 |
| Lng AC66 | Lung 4 | 29 | 137 |
| Mam 59X | Mammary Gland 1 | 56 | 0 |
| Mam B011X | Mammary Gland 2 | 54 | 31 |
| Mam A06X | Mammary Gland 3 | 12 | 0 |
| Ovr 103X | Ovary 1 | 37 | 0 |
| Pan 71XL | Pancreas 1 | 13203 | 4163 |
| Pan 82XP | Pancreas 2 | 39.1 | 0 |
| Pro 12B | Prostate 1 | 386 | 88 |
| Pro 23B | Prostate 2 | 250 | 23 |
| Pro 13XB | Prostate 3 | 92 | 731 |

TABLE 7-continued

Relative levels of Cln108 Expression in Individual Samples

| Sample ID | Tissue | Cancer | Matching Normal Adjacent |
|---|---|---|---|
| Pro 34B | Prostate 4 | 33.3 | 265.7 |
| Pro 20XB | Prostate 5 | 454.6 | 1908.9 |
| Pro 65XB | Prostate 6 | 733.5 | 922.0 |
| End 8XA | Endometrium 1 | 5 | 92 |
| Utr 85XU | Uterus 1 | 98.9 | 21.8 |
| Utr 23XU | Uterus 2 | 35.3 | 0 |
| Utr 135XO | Uterus 3 | 39.2 | 43.8 |
| Utr 141XO | Uterus 4 | 212.1 | 55.9 |

0 = Negative

When matching samples were analyzed, the higher levels of expression were in colon and stomach, showing a high degree of tissue specificity for these two tissues. These results confirm the tissue specificity results obtained with normal pooled samples (Table 6). Furthermore, the level of mRNA expression in cancer samples and the isogenic normal adjacent tissue from the same individual were compared. This comparison provides an indication of specificity for the cancer stage (e.g. higher levels of mRNA expression in the cancer sample compared to the normal adjacent). Table 7 shows overexpression of CSG Cln108 (SEQ ID NO:5) in 13 colon cancer tissues compared with their respective normal adjacent (colon samples #1, 5, 6, 7, 8, 9, 10, 11, 12, 13, 18, 21, and 22). There is overexpression in the cancer tissue for 56% of the colon matching samples tested (total of 23 colon matching samples). The matching sample Pan 71XL is a secondary cancer in pancreas, the primary cancer in that individual was a duodenal cancer.

Altogether, the high level of tissue specificity, plus the mRNA overexpression in more than half of the colon, stomach, and small intestine matching samples tested are demonstrative of this CSG, Cln108 (SEQ ID NO:5), also being a diagnostic marker for colon cancer.

Measurement of SEQ ID NO:7; Clone ID 2348122; Gene ID 23371 (Cln109)

The absolute numbers depicted in Table 8 are relative levels of expression of CSG Cln109 (SEQ ID NO:7) in 12 normal different tissues. All the values are compared to normal ovary (calibrator). These RNA samples are commercially available pools, originated by pooling samples of a particular tissue from different individuals.

TABLE 8

Relative levels of Cln109 Expression in Pooled Samples

| Tissue | NORMAL |
|---|---|
| Colon-Ascending | 28.8 |
| Endometrium | 0.45 |
| Kidney | 0.41 |
| Liver | 0.72 |
| Ovary | 0.07 |
| Pancreas | 82.8 |
| Prostate | 124.3 |
| Small Intestine | 626.4 |
| Spleen | 1.2 |
| Stomach | 12.05 |
| Testis | 1.51 |
| Uterus | 52.99 |

The relative levels of expression in Table 8 show that mRNA expression of CSG Cln109 (SEQ ID NO:7), is more than 5 fold higher in the pool of normal small intestine (626.4) compared to the expression level in any other tissue analyzed. These results demonstrate that Cln109 (SEQ ID NO:7) mRNA expression is highly specific for small intestine.

The absolute numbers in Table 8 were obtained analyzing pools of samples of a particular tissue from different individuals. They can not be compared to the absolute numbers originated from RNA obtained from tissue samples of a single individual in Table 9.

The absolute numbers depicted in Table 9 are relative levels of expression of Cln109 (SEQ ID NO:7) in 53 pairs of matching samples. All the values are compared to normal ovary (calibrator). A matching pair is formed by mRNA from the cancer sample for a particular tissue and mRNA from the normal adjacent sample for that same tissue from the same individual.

TABLE 9

Relative levels of Cln109 Expression in Individual Samples

| Sample ID | Tissue | Cancer | Matching Normal Adjacent |
|---|---|---|---|
| Sto AC93 | Stomach 1 | 2574 | 1310 |
| Sto AC99 | Stomach 2 | 4153 | 5 |
| Sml 21XA | Small Intestine 1 | 2667 | 13663.8 |
| Sml H89 | Small Intestine 2 | 57.8 | 904.29 |
| Cln B56 | Colon-Cecum (A) 1 | 6794 | 299 |
| Cln AS45 | Colon-Ascending (A) 2 | 814.6 | 105.8 |
| Cln CM67 | Colon-Cecum (B) 3 | 294.6 | 36.1 |
| Cln AS67 | Colon-Ascending (B) 4 | 2.2 | 26.3 |
| Cln AS43 | Colon-Ascending (C) 5 | 111 | 377 |
| Cln AS46 | Colon-Ascending (C) 6 | 1180 | 352 |
| Cln AS98 | Colon-Ascending (C) 7 | 1075 | 92 |
| Cln AS89 | Colon-Ascending (D) 8 | 14022.7 | 87.5 |
| Cln TX01 | Colon-Transverse (B) 9 | 1027.6 | 282.1 |
| Cln TX89 | Colon-Transverse (B) 10 | 2.5 | 23.7 |
| Cln TX67 | Colon-Transverse (C) 11 | 0.1 | 72.3 |
| Cln MT38 | Colon-Splenic Flexture (M) 12 | 372 | 88 |
| Cln SG89 | Colon-Sigmoid (B) 13 | 179.2 | 33.4 |
| Cln SG67 | Colon-Sigmoid (C) 14 | 85.0 | 94.7 |
| Cln SG33 | Colon-Sigmoid (C) 15 | 5461 | 377 |
| Cln SG45 | Colon-Sigmoid (D) 16 | 762.7 | 15.9 |
| Cln B34 | Colon-Rectosigmoid (A) 17 | 460 | 1 |
| Cln RC67 | Colon-Rectum (B) 18 | 64.5 | 136.2 |
| Cln C9XR | Colon-Rectosigmoid (C) 19 | 441 | 34 |
| Cln RS45 | Colon-Rectosigmoid (C) 20 | 1931 | 195 |
| Cln RC01 | Colon-Rectum (C) 21 | 72.8 | 19.1 |
| Cln RC89 | Colon-Rectum (D) 22 | 4.8 | 90.2 |
| Bld 46XK | Bladder 1 | 4 | 3 |
| Bld 66X | Bladder 2 | 1 | 0 |
| Bld 32XK | Bladder 3 | 0.1 | 307.6 |
| Kid 126XD | Kidney 1 | 0 | 2 |
| Kid 12XD | Kidney 2 | 3 | 16 |
| Kid 5XD | Kidney 3 | 0.0 | 0.3 |
| Kid 6XD | Kidney 4 | 18.5 | 1.2 |
| Liv 42X | Liver 1 | 21 | 0.03 |

TABLE 9-continued

Relative levels of Cln109 Expression in Individual Samples

| Sample ID | Tissue | Cancer | Matching Normal Adjacent |
|---|---|---|---|
| Liv 15XA | Liver 2 | 0.5 | 0.4 |
| Liv 94XA | Liver 3 | 0.4 | 0.0 |
| Lng AC69 | Lung 1 | 0.1 | 0 |
| Lng BR94 | Lung 2 | 3 | 0 |
| Lng 60XL | Lung 3 | 0.1 | 0 |
| Mam 59X | Mammary Gland 1 | 0 | 4 |
| Mam B011X | Mammary Gland 2 | 8 | 13 |
| Mam A06X | Mammary Gland 3 | 4.7 | 9.6 |
| Pan 71XL | Pancreas 1 | 8902.5 | 1428.2 |
| Pan 82XP | Pancreas 2 | 0.2 | 9.3 |
| Pro 12B | Prostate 1 | 9 | 20 |
| Pro 23B | Prostate 2 | 191 | 88 |
| Pro 13XB | Prostate 3 | 12 | 460 |
| Pro 34B | Prostate 4 | 3.2 | 80.4 |
| Tst 39X | Testis 1 | 29.9 | 0 |
| End 8XA | Endometrium 1 | 0.3 | 21 |
| Utr 85XU | Uterus 1 | 244.7 | 592.2 |
| Ovr 63A | Ovary 1 | 11.4 | 0 |
| Ovr A1C | Ovary 2 | 68.4 | 0 |

0 = Negative

When matching samples were analyzed, the higher levels of expression were in small intestine, colon and stomach, showing a high degree of tissue specificity for these three colon tissues. These results confirm the tissue specificity results obtained with normal pooled samples for small intestine (Table 8). Furthermore, the level of mRNA expression in cancer samples and the isogenic normal adjacent tissue from the same individual were compared. This comparison provides an indication of specificity for the cancer stage (e.g. higher levels of mRNA expression in the cancer sample compared to the normal adjacent). Table 9 shows overexpression of CSG, Cln109 (SEQ ID NO:7) in 15 colon cancer tissues compared with their respective normal adjacent (colon samples #1, 2, 3, 6, 7, 8, 9, 12, 13, 15, 16, 17, 19, 20, and 21). There is overexpression in the cancer tissue for 68% of the colon matching samples tested (total of 22 colon matching samples). The matching sample Pan 71XL is a secondary cancer in pancreas, the primary cancer in that individual was a duodenal cancer.

Altogether, the high level of tissue specificity, plus the mRNA overexpression in more than half of the colon, stomach, and small intestine matching samples tested are demonstrative of CSG Cln109 (SEQ ID NO:7) being a diagnostic marker for colon cancer. The amino acid sequence encoded by the open reading frame of Cln109 is depicted in SEQ ID NO:10.

What is claimed is:

1. A method for detecting colon cancer in a patient comprising:
   (a) measuring levels of a polynucleotide comprising SEQ ID NO:3 or native protein encoded by SEQ ID NO:3 in a sample of cells, tissue or bodily fluid obtained from the patient; and
   (b) comparing the measured levels of the polynucleotide comprising SEQ ID NO:3 or the native protein encoded by SEQ ID NO:3 with levels of the polynucleotide comprising SEQ ID NO:3 or the native protein encoded by SEQ ID NO:3 in a sample of cells, tissue or bodily fluid obtained from a control, wherein an increase in measured levels of the polynucleotide comprising SEQ ID NO:3 or the native protein encoded by SEQ ID NO:3 in the patient versus the levels of the polynucleotide comprising SEQ ID NO:3 or the native protein encoded by SEQ ID NO:3 in the control is associated with the presence of colon cancer.

2. The method of claim 1 wherein the sample is cells.

3. The method of claim 1 wherein the sample is tissues.

4. The method of claim 1 wherein the sample is bodily fluids.

5. The method of claim 1 wherein levels of the polynucleotide comprising SEQ ID NO:3 are measured.

6. The method of claim 5 wherein the sample is cells.

7. The method of claim 5 wherein the sample is tissues.

8. The method of claim 5 wherein the sample is bodily fluids.

9. The method of claim 1 wherein levels of the native protein encoded by SEQ ID NO:3 are measured.

10. The method of claim 9 wherein the sample is cells.

11. The method of claim 9 wherein the sample is tissues.

12. The method of claim 9 wherein the sample is bodily fluids.

* * * * *